United States Patent [19]
Yu et al.

[11] Patent Number: 6,090,972
[45] Date of Patent: Jul. 18, 2000

[54] CRYSTALLIZATION OF α-L-ASPARTYL-L-PHENYLALANINE METHYL ESTER

[75] Inventors: See Young Yu, Seoul; Jin Man Cho, Kyungki-do; Bun Sam Lim, Seoul, all of Rep. of Korea

[73] Assignee: Daesang Corporation, Rep. of Korea

[21] Appl. No.: 09/356,663

[22] Filed: Jul. 19, 1999

Related U.S. Application Data

[63] Continuation of application No. 09/191,055, Nov. 12, 1998.

[51] Int. Cl.⁷ .................................................. C07C 227/42
[52] U.S. Cl. ................................................................ 560/41
[58] Field of Search ................................................. 560/41

[56] References Cited

U.S. PATENT DOCUMENTS

| | | | |
|---|---|---|---|
| 5,425,787 | 6/1995 | Abe et al. | 23/295 R |
| 5,543,554 | 8/1996 | Ohura et al. | 560/41 |

FOREIGN PATENT DOCUMENTS

| | | |
|---|---|---|
| 0 399 605 A1 | 11/1990 | European Pat. Off. . |
| 0 405 2773 A2 | 1/1991 | European Pat. Off. . |
| 0 484 769 A2 | 5/1992 | European Pat. Off. . |
| 0 547 342 A1 | 6/1993 | European Pat. Off. . |
| 0 733641 A1 | 9/1996 | European Pat. Off. . |

*Primary Examiner*—Samuel Barts
*Attorney, Agent, or Firm*—Knobbe, Martens, Olson & Bear LLP

[57] ABSTRACT

Disclosed is a method of cooling and crystallizing α-L-aspartyl-L-phenylalanine methyl ester, which is a sweetening agent, commonly referred to as aspartame. An aspartame solution is cooled such that the solution is flown while being continuously in thermal contact with a coolant. As the cooling of the aspartame solution by the thermal contact with the coolant proceeds, the temperature difference between the aspartame solution and the coolant remains substantially constant. The coolant flows in the opposite direction as the aspartame solution flows and cools an upstream part of the aspartame solution as the coolant flows downstream.

34 Claims, 5 Drawing Sheets

CRYSTALLIZATION OF α-L-ASPARTYL-L-PHENYLALANINE METHYL ESTER

RELATED APPLICATIONS

This application is a continuation of application Ser. No. 09/191,055 filed Nov. 12, 1998, now allowed.

BACKGROUND OF THE INVENTION

1. Field of the Invention

The present invention relates to producing a low-calorie sweetening substance, more particularly, to crystallization of the α-L-aspartyl-L-phenylalanine methyl ester.

2. Description of the Related Technology

α-L-aspartyl-L-phenylalanine methyl ester, hereinafter referred to as aspartame, is a low-calorie sugar substitute and is industrially synthesized in several different processes. The synthesized aspartame in solution is then isolated most commonly by crystallization followed by dewatering and drying processes. Further treatments or processes can be applied to the aspartame to provide various consumer products.

Crystallization occurs by cooling a solution or by evaporating the solvent thereof In cooling crystallization, as the solution is cooled, the solute, herein aspartame, is supersaturated, which causes formation and growth of crystals. Generally, obtaining coarse and uniform crystals is the goal. In theory, this can be accomplished by cooling the solution with an infinitesimal amount of heat transfer, which would take a very long period of time.

In practice, an aspartame solution is cooled and the crystallization is carried out by heat exchanging the solution with a coolant having a significantly lower temperature than the solution. The temperature of the solution is readily homogenized by stirring or agitating the solution, in which the time for crystallization is reduced. However, the cooling with a relatively large temperature difference does not produce coarse and uniform crystals.

Further, U.S. Pat. No. 5,543,554 discusses that forced flow or agitation of the aspartame solution during the cooling crystallization deteriorates crystal properties in removing liquid therefrom. Based on this, the patent suggests that no forced flow or agitation has to be applied during the crystallization of the aspartame. However, the cooling is commonly carried out by heat-exchange between the aspartame solution and a coolant via a surface. Without forced flow or agitation, local crystallization occurs near the heat-exchange surface before the temperature of the solution is homogenized. The locally formed crystals are likely to precipitate on the surface and form scales. The scales in turn deteriorate the cooling efficiency of the solution by acting as an insulating layer, as well as require laborious work to remove afterward.

SUMMARY OF THE INVENTION

One aspect of the present invention provides a method of crystallizing aspartame. The method comprises providing an aqueous solution of the aspartame; flowing the aspartame solution in a first direction; and flowing a coolant in a second direction opposite to the first direction through a coolant passage provided along the flow of the aspartame solution. The coolant passing through the coolant passage is in thermal contact with the aspartame solution, whereby the aspartame solution is cooled and the aspartame dissolved therein crystallizes.

Another aspect of the present invention provides a method of cooling an aqueous of aspartame. The method comprises flowing the aspartame solution continuously in thermal contact with a coolant. As the cooling of the aspartame solution proceeds, a temperature difference between the aspartame solution and the coolant remains substantially constant.

These and other features of the present invention will become more fully apparent from the following description and claims.

DETAILED DESCRIPTION OF THE PREFERRED EMBODIMENT

In cooling crystallization, heat-exchange takes place between an aspartame solution and a coolant via a cooling or heat transfer surface. If the coolant is cool enough to crystallize the aspartame, some aspartame instantly crystallizes when the solution contacts the surface and forms scales on the surface. The solution temperature gradually decreases by the heat-exchange with the coolant from near the surface to the entire solution. Accordingly, aspartame crystals generate little by little from near the heat transfer surface.

Small aspartame crystals attract one another and tend to form crystal lumps. The crystals and crystal lumps (collectively "crystals") retain aspartame solution within the structure thereof and do not automatically separate from the solution by the difference of its specific gravity. Instead, the crystals are suspended in the solution. These crystals show very low mobility and are likely to stay where they were crystallized or formed lumps, mostly near the heat transfer surface.

Since the aspartame crystals have a relatively low heat conductivity, those precipitated on or suspended near the surface may heat-insulate or hinder the heat transfer through the entire solution. Moreover, since the crystals formed near the surface do not move well, there is a possibility that they precipitate on the surface and form scales thereon. Once the crystals precipitate on the surface in addition to the instant formation of scales, they further block heat-exchange between the solution and surface and laborious work will be required to remove it later on.

To avoid the instant formation of scales on the cooling surface and to form coarse and uniform crystals, the temperature difference between the coolant and the solution should be controlled. Also, in order to avoid the occurrence of heat insulation of the suspended crystals as well as further formation of scales, forced flow of the aspartame solution and the crystals should be considered during the cooling crystallization, regardless of the suggestion provided by the prior art.

According to the present invention, the temperature is controlled in such a manner that temperature difference between the coolant and the solution is kept as small as possible during the whole crystallization process. The control can be achieved by providing a continuous heat-exchange between the coolant and the aspartame solution.

During the whole process of the cooling crystallization, the coolant becomes gradually warmer as the heat-exchange goes on, but the coolant keeps its temperature a little lower than that of the aspartame solution. The warmest coolant, which has heat-exchanged with cooler solutions, cools the warmest aspartame solution, which is freshly fed into the cooling crystallization. Also, the coolest coolant, which is freshly supplied to the heat-exchange, cools the coolest slurry, which includes aspartame crystals suspended in the remaining aspartame solution.

Alternatively, the small temperature difference between the coolant and the aspartame solution may be achieved by providing a coolant, which is gradually getting cooler with a temperature a little lower than the solution temperature all over the cooling process.

According to the present invention, the aspartame solution under the cooling crystallization is continuously agitated or stirred. The agitation or stir of the aspartame solution distribute crystals over the solution, which prevents the heat insulation by the crystals near the surface and the formation of scales by the crystals thereon. The agitation or stir can also homogenize the temperature and the concentration of the solution, which enhances the cooling crystallization of the aspartame over the whole solution, not only near the cooling surfaces. However, since drastic stir or agitation of the solution may result in breakdown of coarse crystal lumps and may also prevent growth of crystals, a moderate agitation or stir is required.

According to one embodiment of the present invention, the coolant and the aspartame solution pass by in the opposite direction and heat-exchange with each other. A crystallizer schematically illustrated in FIG. 1 can be used in the cooling crystallization in accordance with one embodiment of the present invention. The crystallizer 10 has a cooling compartment 12, within which the cooling crystallization of aspartame is carried out. The cooling compartment include an inlet 14 to feed aspartame solution into the compartment 12. An outlet 16 is also provided at a farthest end of the cooling compartment 12 from the inlet 14. Advantageously, the cooling compartment 12 of the crystallizer 10 extends longitudinally straightly between the inlet side and outlet side. The crystallizer 10 has at least one coolant passage, through which a coolant passes.

Figure 1:
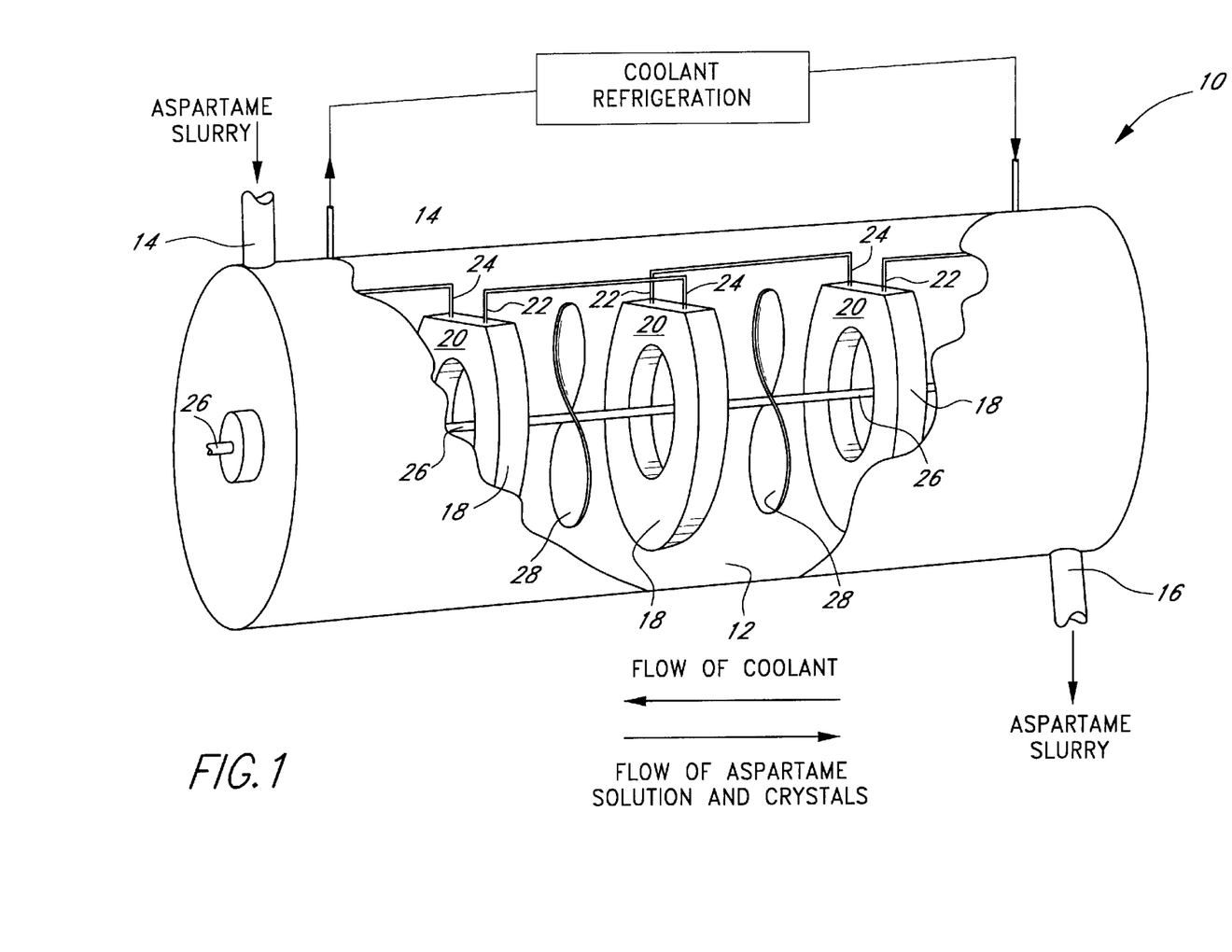
FIG. 1 shows a schematic crystallizer to be used in cooling crystallizing the aspartame in accordance with the present invention.

The aspartame solution is continuously fed into the cooling compartment 12 through the inlet 14 and flows from the inlet side toward the outlet side of the cooling compartment 12. The aspartame solution in the flow toward the outlet is gradually cooled by heat-exchange with the coolant in the manner as will be described below. Near the outlet 16 in the cooling compartment 12, a considerable amount of the aspartame exists in the form of crystal and forms slurry with the residual solution. The aspartame slurry is then discharged through the outlet 16.

Through the coolant passage, the coolant is introduced into the cooling compartment 12 near the slurry outlet 16. Advantageously, the coolant is flowing into the cooling compartment at a location closer to the slurry outlet 16 than a quarter distance between the inlet 14 and outlet 16 from the outlet 16. The coolant thermally contacts the aspartame solution through the coolant passage.

Advantageously, a series of heat-exchange tubes 18 are installed in line at an interval within the cooling compartment 12 of the crystallizer 10. Each tube 18 includes heat-exchange surfaces 20, a coolant inlet 22 and a coolant outlet 24. The coolant outlet 24 of each tube 18 is in fluid communication with the coolant inlet 22 of the solution supply side neighboring tube 18, by which the coolant flows in the opposite direction of the aspartame solution flow. The coolant flows into each tube 18 through the coolant inlet 22 and heat-exchanges with the solution via the surfaces 20.

Since the coolant passes through the coolant passage in the opposite direction of the solution, the coolant flows from the outlet side toward the inlet side of the cooling compartment 12. The coolant introduced in to the cooling compartment, near the slurry outlet 16, first heat-exchanges with the coolest part of the solution, which is the slurry and about to be discharged as discussed above. As the coolant passes through the passage toward the inlet side and heat-exchanges with the aspartame solution, the coolant becomes warmer. Near the aspartame solution inlet 14 of the cooling compartment 12, the coolant becomes the warmest but is still cooler than and heat-exchanges with the aspartame solution being fed through the inlet 14.

The coolant which has completed the heat-exchange with the solution flows out of the cooling compartment near the solution inlet 14. Advantageously, the coolant is discharged from the cooling compartment at a location closer to the solution inlet 14 than a quarter distance between the inlet 14 and outlet 16 from the inlet 14. The coolant advantageously then goes to the remainder of its refrigeration cycle outside the cooing compartment 12 and returns back into the passage near the slurry outlet 16 of the cooling compartment 12.

Figure 2:
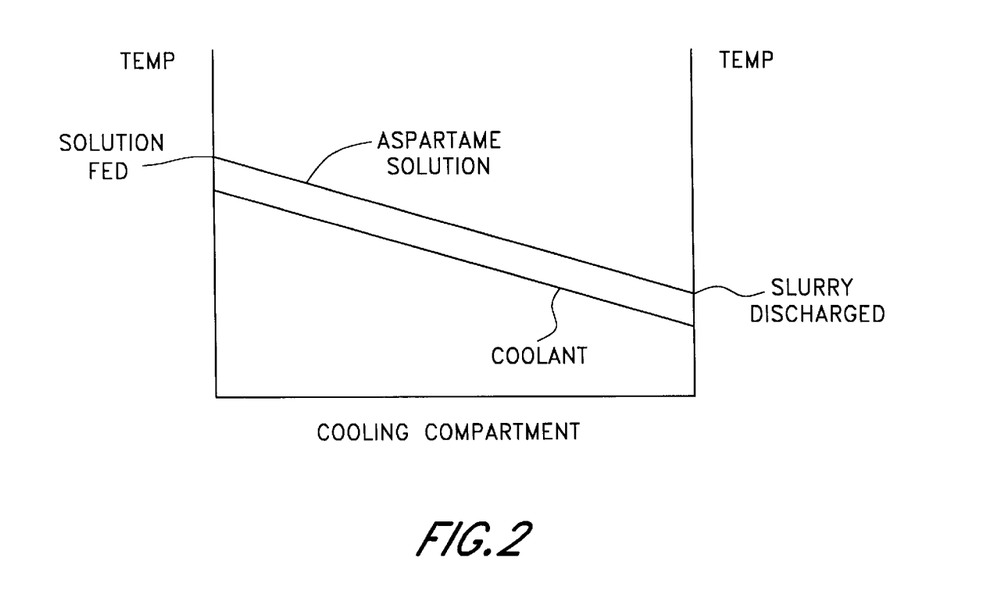
FIG. 2 shows the temperatures of the aspartame solution and the coolant along the length of the crystallizer, illustrating the constant temperature difference of the solution and the coolant.
Figure 3:
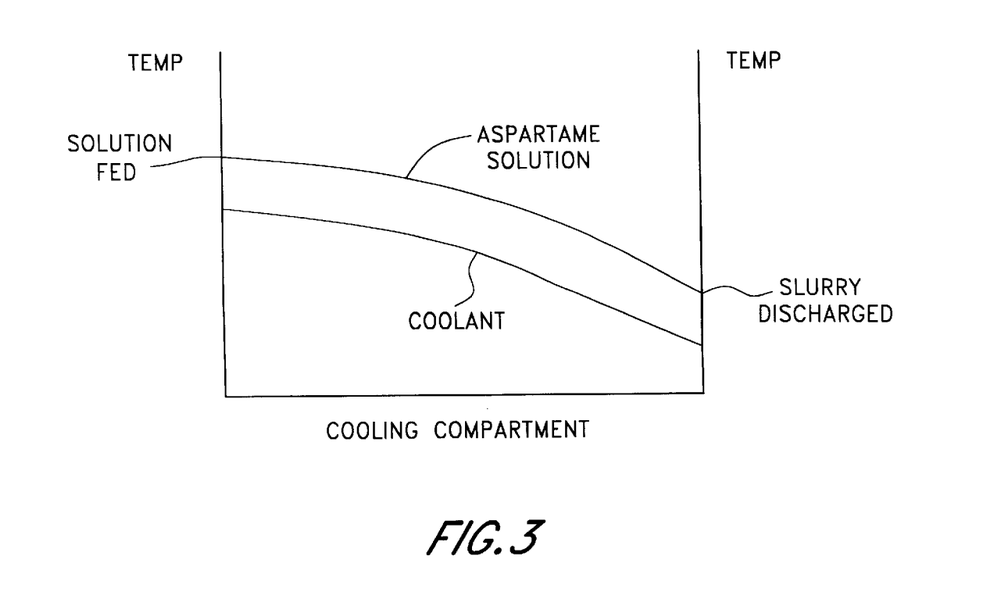
FIG. 3 shows the temperatures of the aspartame solution and the coolant along the length of the crystallizer, illustrating the varying temperature difference of the solution and the coolant.

FIG. 2 illustrates the temperature difference between the coolant and the aspartame solution in the cooling crystallization according to one embodiment of the present invention. The opposite flows of the coolant and the aspartame solution enable the temperature difference thereof in heat-exchange to be small. The temperature difference between the coolant and the solution at any locations along the aspartame flow remains almost constant. In other words, the cooling is carried out with an almost constant and small amount of heat transfer from the aspartame solution to the coolant. Alternatively, the temperature difference between the coolant and the aspartame solution can vary. FIG. 3 shows the change of temperature difference by changing coolants at a location between the solution inlet 14 and slurry outlet 16 of the cooling compartment 12.

The small temperature difference minimizes the instant precipitation of aspartame crystals and formation of scales onto the heat transfer surfaces. This, in turn, is helpful to homogeneously cool the whole aspartame solution. Further, since the temperature of the aspartame solution is gradually and smoothly lowered, the crystals are coarser and more uniform than obtained by drastic heat-exchange.

Homogeneous cooling as well as constant and small temperature difference can advantageously be facilitated by providing as many and large heat-exchange surfaces as possible. Also, as a natural consequence, the large and many surfaces shorten the time required in the cooling crystallization.

As discussed above, since the aspartame crystals have very low mobility, they stay near the location where they crystallize. Although the aspartame solution is continuously fed through the solution inlet 14, the crystals are not likely move or flow well. According to one embodiment of the present invention, the aspartame solution is continuously agitated or stirred during the whole cooling crystallization.

Referring back to FIG. 1, an agitator or stirrer is provided within the cooling compartment 12 to forcedly stir and flow the crystals toward the slurry outlet 16 thereof. A rotating shaft 26 and at least one fan 28 attached thereto form the agitator or stirrer. Advantageously, the shaft 26 of the agitator or stirrer extends longitudinally along the extension of the crystallizer 10. Advantageously, a plurality of fans 28 attached along the shaft 26 at an interval to effectively generate the current or flow of the solution and the crystals. The plurality of fans 28 are advantageously formed between neighboring heat-exchange tubes 18 at the same interval as the tubes 18. Each tube 18 has a hole for extending the shaft 26 as well as for facilitating the flow of the aspartame solution and crystals. Although not illustrated, each fan 28 advantageously has a scraper at the distal end thereof to remove scales, which may deposit on the heat-exchange surfaces 20 as well as the inner surface of the cooling compartment 12.

The crystals formed are forced to move toward the outlet side of the cooling compartment 12, where the slurry is discharged. Thus, the forced agitation makes the supply of the solution and the discharge of the slurry easy, which forms a steady flow of the aspartame solution in the cooling compartment 12. Since the crystals suspended near the heat-exchange surfaces 20 or the inner surface of the compartment 12 are moving, the formation of scales on these surfaces are also inhibited. Further, with the scraper provided on the distal end of each fan 28, scales formed on these surfaces are effectively removed.

In accordance with the present invention, an aspartame aqueous solution to be crystallized is prepared. Water or a mixture of water and lower alcohol, such as methanol, ethanol, isopropanol, or t-butanol is advantageously used as a solvent. Other water-miscible organic solvents can also be used.

Before the crystallization, the aspartame aqueous solution is heated to adjust the concentration high enough to obtain a decent amount of aspartame crystals in the cooling crystallization. The aspartame solution is heated until aspartame begins to break down and forms benzyl-3,6-dioxo-2-piperazine acetic acid or α-L-aspartyl-L-phenylalanine, which is at about 70° C. The initial temperature of the aspartame solution supplied to the crystallization is advantageously from about 30° C. to about 70° C. Desirably, the solution is supplied into the inlet at about 40° C. to about 60° C.

The aspartame solution is continuously cooled by the coolant in a controlled manner as described above. As the temperature decreases, the solubility of the aspartame in water or aqueous solution sharply decreases and the aspartame dissolved in the solution crystallizes well. When the temperature of the solution reaches about 10° C., the solubility does not change that rapidly as the temperature changes. The amount of aspartame in the solution itself becomes small due to the deposition of the crystals by then. In this respect, the aspartame solution is advantageously cooled down to about 20° C., and the slurry is discharged. The cooling crystallization is carried out desirably until about 8° C.

A coolant is selected, considering the feeding and discharging temperatures of the aspartame in the cooling crystallization. Any coolants which can absorb heat between about −5° C. and about 55° C. can be used in the cooling crystallization in accordance with the present invention. Advantageously, brine water or aqueous solution of ethylene glycol or propylene glycol is used as a coolant. Plain water can also be used in case the entire cooling process is carried out above 0° C. The coolant passing through the passage near the slurry outlet is from about −5° C. to about 10° C. The temperature of the coolant near the solution inlet is from about 35° C. to about 55° C.

Advantageously, the temperature difference between the coolant and the solution is controlled by varying the flow rate of the coolant through the passage. As discussed above, the temperature difference is advantageously maintained almost constant along the length of the crystallizer. Alternatively, the temperature difference can be varied along the length of the crystallizer by adjusting the flow rate of the coolant to vary. Advantageously, the coolant flow rate is adjusted so that a larger temperature difference is maintained near the outlet side of the crystallizer.

The temperature difference is advantageously as small as possible to obtain coarse and uniform crystals as discussed above. However, if the temperature difference is infinitesimally small, it would take too long period of time in the crystallization process. To reduce the time, a definite amount of temperature difference exists. The temperature difference advantagesouly remains constant along the entire cooling compartment, as discussed above in connection with FIG. 2. Advantageously, the temperature difference is from about 5° C. to about 15° C., and preferably it is about 5–7° C.

Heat insulation is advantageously provided to the crystallizer to avoid any uncontrolled heat-exchange. Advantageously, an insulating material wraps the outside of the crystallizer, which prevents possible heat-exchange between the outside atmosphere of the crystallizer and the aspartame solution or the coolant.

The agitator advantageously stirs the solution and crystals slowly enough not to re-dissolve or break down the crystals formed. The shaft of the agitator advantageously rotates at about 0.1–10 rpm, and desirably at about 0.5–3 rpm.

The aspartame solution is continuously fed through the inlet at a rate of about 500–2,000L/Hr. The solution and crystals are forcedly flown toward the slurry outlet 16 within the cooling compartment 12. The slurry is discharged through the outlet 16 at the same rate of the aspartame solution feeding into the cooling compartment 12.

After the cooling crystallization, the residual mother liquid in the slurry separated from the solid aspartame crystals. The mother liquid is advantageously reused in the preparation of the aspartame hydrochloric acid solution after purification. To remove the liquid from the slurry, various techniques, such as centrifugation, vacuum filtration, pressure filtration, etc., can be utilized. Sometimes, the liquid retained within the crystal structure is not easily separated. The slurry is optionally stirred more drastically than the agitation during the crystallization to facilitate the removal of the liquid. When the solid aspartame crystals are separated by removing the liquid, the solid aspartame crystals are dried to reduce moisture content within the crystal structure.

Now the present invention will be further described in terms of the following examples, which are intended to illustrate and do not limit the present invention.

EXAMPLE 1

This experiment was conducted using an "Cooling Disc Crystallizer" available from GMF Gouda Company. The structure and operation of the crystallizer are disclosed in U.S. Pat. No. 4,486,395, which is herein incorporated by reference.

An aspartame aqueous solution for crystallization was prepared, and the initial concentration of aspartame dissolved in the solution was adjusted to 4 wt. % at 60° C. The prepared aspartame solution was introduced into the cooling compartment through the inlet at a rate of 1,000 L/Hr. Brine water was used as a coolant. The coolant was introduced into the compartment near the slurry outlet at 10° C. The temperature difference between the coolant and the solution was adjusted to 15° C. 4 hours' steady flow with rotation speed of 0.5 rpm of the shaft was maintained. The slurry was discharged through the outlet at 25° C. The slurry was further cooled to 8° C. to further crystallize the aspartame which is still dissolved in the slurry. The thus obtained slurry was dewatered by centrifugation with 600 G-Force. The dewatered aspartame crystals were measured the moisture content of 39.5 wt. %.

EXAMPLE 2

The same experiment as in Example 1 was repeated except that the coolant flow rate was adjusted to make the temperature difference of the coolant and the solution to be about 10° C. and that the steady flow was maintained for 3 hours with rotation speed of 1 rpm of the shaft. The dewatered aspartame crystals obtained had moisture content of 36.4 wt. %.

EXAMPLE 3

The same experiment as in Example 2 was repeated except that the temperature difference between the solution and the coolant was kept differently within the crystallizer and that the steady flow was maintained for 3 hours with rotation speed of 1 rpm of the shaft. The coolant is supplied into the crystallizer such that the temperature difference in the solution inlet side half of the crystallizer is kept about 5° C. and the temperature difference of the other half is kept about 7° C. The dewatered aspartame crystals obtained had moisture content of 38.5 wt. %.

COMPARATIVE EXAMPLE 1

An aspartame aqueous solution for crystallization was prepared, and the initial concentration of aspartame dissolved in the solution was adjusted to 4 wt. % at 60° C. 1,000 L of the prepared aspartame solution was introduced into a crystallizing vessel, which has a crystallizing vessel, a plurality of jackets around the vessel, a rotating agitator provided into the vessel. 5° C. water was supplied to the jackets to cool the aspartame solution contained in the vessel by conductive heat exchange. The aspartame solution was cooled to 8° C. with forced flow or agitation by the agitator rotating at 25 rpm, thereby aspartame dissolved in the solution crystallized. The obtained slurry was dewatered by centrifugation with 600 G-Force. The dewatered aspartame crystals were measured the moisture content of 49.2 wt. %.

COMPARATIVE EXAMPLE 2

An aspartame aqueous solution for crystallization was prepared, and the initial concentration of aspartame dissolved in the solution was adjusted to 4 wt. % at 60° C. 1,000 L of the prepared aspartame solution was introduced into a crystallizer which has a crystallizing vessel, a plurality of plates within the vessel and a plurality of jackets around the vessel. 5° C. water was supplied to the plates and jackets to cool the aspartame solution contained in the vessel by conductive heat exchange. The aspartame solution was cooled to 25° C. without any forced flow or agitation of the solution, thereby aspartame dissolved in the solution crystallized. The crystallized aspartame and the remaining solution were transferred to another vessel, in which they were forcedly stirred by an agitator rotating at 10 rpm to facilitate the separation of solid and liquid phases in the following step while being further cooled to 8° C. The obtained slurry was dewatered by centrifugation with 600 G-Force. The dewatered aspartame crystals were measured the moisture content of 39.8 wt. %.

COMPARATIVE EXAMPLE 3

The same crystallizer as used in the experiment of Example 1 was used. 4 wt. % aspartame water solution at 60° C. was continuously fed into the cooling compartment through the inlet at a rate of 1000 L/Hr. Water solution with 30 wt. % of propylene glycol is used as a coolant. The coolant was introduced into the cooling compartment at 25° C. Aspartame solution was maintained within the cooling compartment for 1 hour with rotation speed of 10 rpm of the shaft. The temperature difference between the coolant and the solution was not controlled. Measured temperature differences between the solution and coolant was 35° C. for the first 20 minutes and maintained between 10–30° C. thereafter. The slurry was discharged and was dewatered by centrifugation with 600 G-Force. The dewatered aspartame crystals were measured the moisture content of 52.8 wt. %.

As seen in the foregoing description and the examples, the present invention provides an improved crystallization of aspartame.

Figure 4:
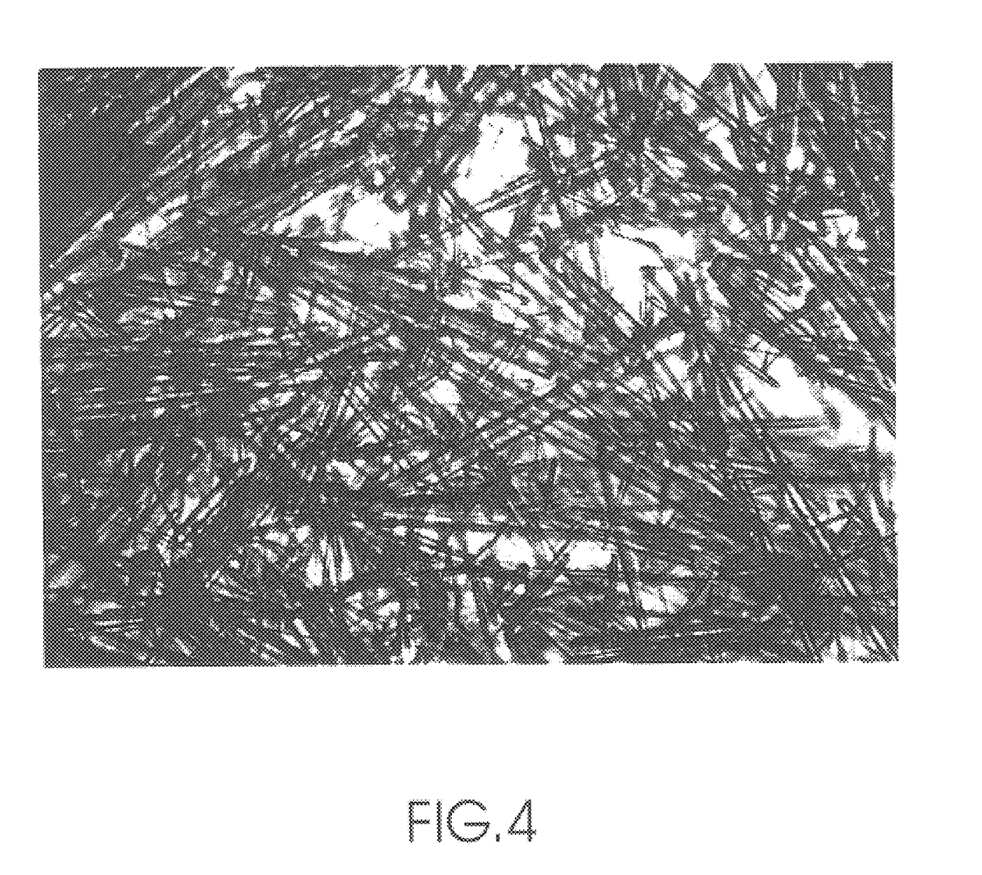
FIG. 4 is a microscopic view (×63) of aspartame crystals obtained in accordance with one embodiment of the present invention.
Figure 5:
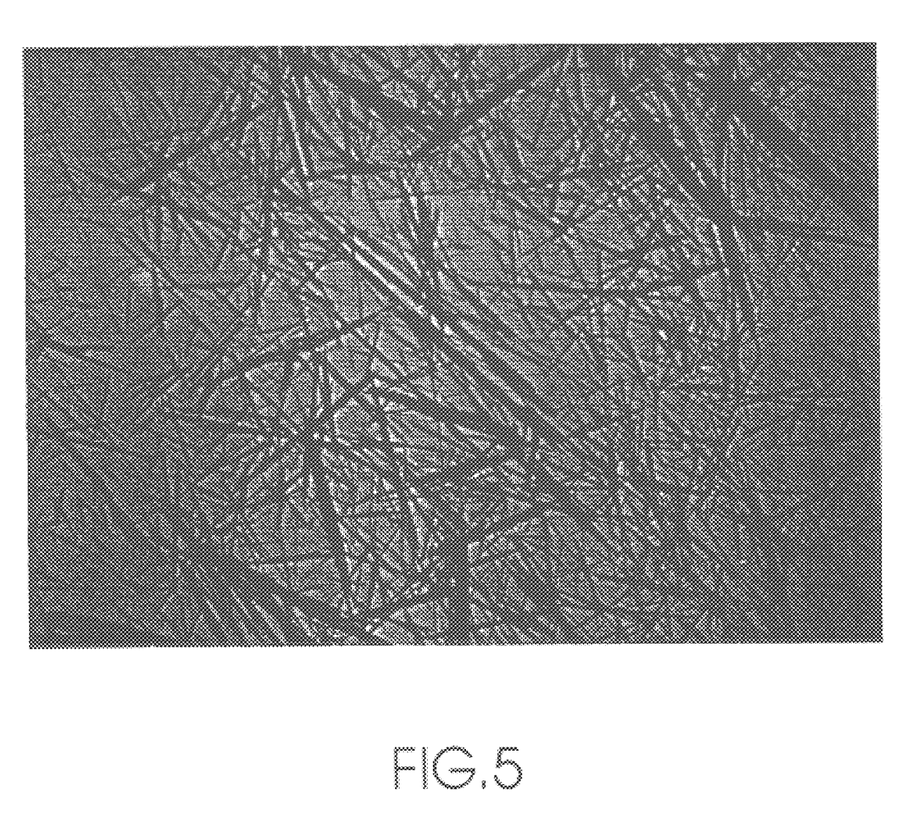
FIG. 5 is a microscopic view (×63) of aspartame crystals produced by a prior art crystallization method with forced agitation or stir.
Figure 6:
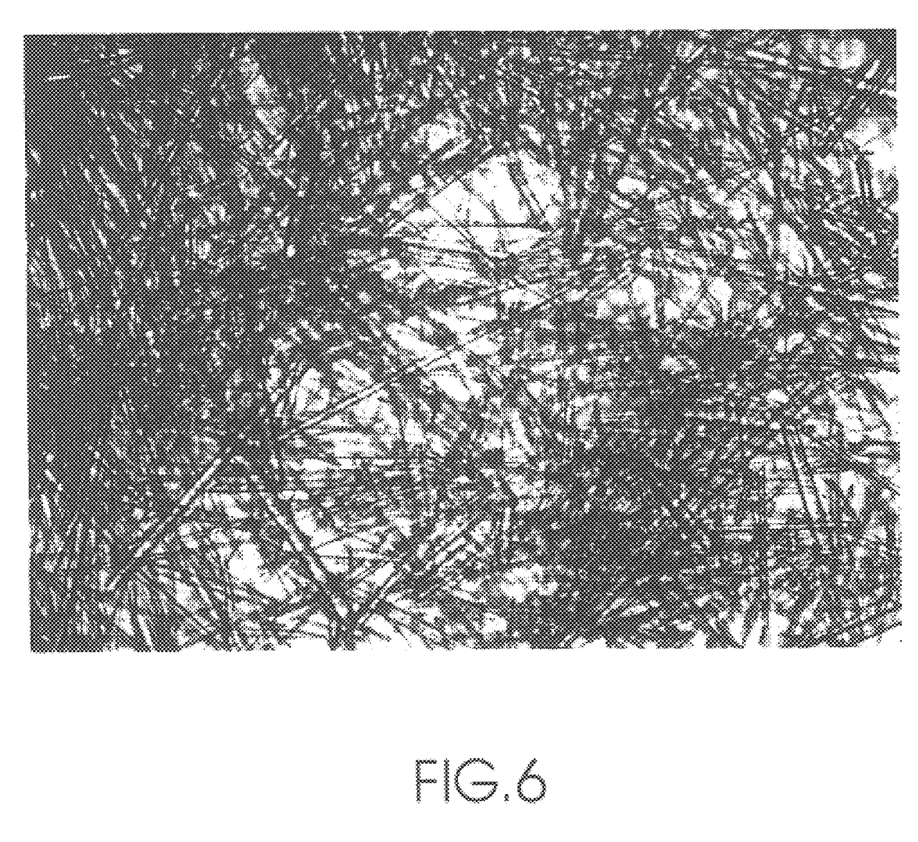
FIG. 6 is a microscopic view (×63) of aspartame crystals produced by a prior art crystallization method without forced agitation or stir.

The aspartame crystals obtained by the crystallization according to the present invention (Examples 1 to 3) have lower moisture contents after the dewatering than the aspartame crystals obtained by conventional crystallization (Comparative Examples 1 and 2). Also, the crystallization with controlled heat-exchange (Examples 1 to 3) produced aspartame having lower moisture contents than the crystallization without controlled heat exchange (Comparative Example 3). Additionally, the aspartame crystals obtained by the crystallization according to the present invention (FIG. 4) are generally coarser and more uniform in their structure than aspartame crystals produced by conventional crystallization methods (FIGS. 5 and 6).

In summary, unlike the aspartame crystals produced by the prior art, the aspartame crystals obtained by the present invention have good dewaterability. Further, the aspartame crystals by the present invention have coarse and uniform structure.

Although the present invention has been described in terms of embodiments, other embodiments will become apparent to those of ordinary skill in the art, in view of the disclosure herein. Accordingly, the present invention is not intended to be limited by the recitation of the embodiments, but is instead intended to be defined solely by reference to the appended claims.

What is claimed is:

1. A method of crystallizing α-L-aspartyl-L-phenylalanine methyl ester (aspartame), comprising:
   providing an aqueous solution of the aspartame;
   flowing the aspartame solution in a first direction; and
   flowing a coolant in a second direction opposite to the first direction through a coolant passage provided along the flow of the aspartame solution, the coolant passing through the coolant passage thermally contacting the aspartame solution, whereby the aspartame solution is cooled and the aspartame dissolved therein crystallizes.

2. A method of cooling an aqueous of aspartame, comprising flowing the aspartame solution continuously in thermal contact with a coolant, wherein a temperature difference between the aspartame solution and the coolant remains substantially constant as the cooling of the aspartame solution proceeds.

3. The method as defined in claim 2, wherein the coolant flows in an opposite direction as the aspartame solution flows and keeps thermal contact with the aspartame solution, whereby the coolant cools an upstream part of the aspartame solution as the coolant flows downstream.

4. A method of crystallizing aspartame, comprising cooling of an aspartame solution according to the method of claim 2 to a temperature at which the aspartame crystallizes.

5. The method as defined in claim 1, wherein temperature difference between the aspartame solution and the coolant remains substantially constant during the whole cooling of the aspartame solution.

6. The method as defined in claim 5 wherein temperature difference between the aspartame solution and the coolant is from about 5° C. to about 15° C.

7. The method as defined in claim 6 wherein the temperature difference between the aspartame solution and the coolant is from about 5 to about 7° C.

8. The method as defined in claim 1, wherein temperature difference between the aspartame solution and the coolant changes during the cooling crystallization of the aspartame solution.

9. The method as defined in claim 1, wherein in the aspartame aqueous solution, aspartame is dissolved in water or water-immiscible organic solvent.

10. The method as defined in claim 1, wherein initial temperature of the aspartame solution is from about 30° C. to about 70° C.

11. The method as defined in claim 1, wherein the aspartame aqueous solution becomes aspartame slurry as the aspartame crystallizes.

12. The method as defined in claim 11, wherein temperature of the aspartame slurry obtained is about 20° C.

13. The method as defined in claim 12, wherein temperature of the aspartame slurry obtained is about 8° C.

14. The method as defined in claim 11, further comprising cooling the obtained aspartame slurry to further crystallize aspartame remaining dissolved in the slurry.

15. The method as defined in claim 1, wherein the coolant used is one selected from the group consisting of water, brine water, and aqueous solution of ethylene glycol or propylene glycol.

16. The method as defined in claim 1, wherein flowing the aspartame solution, flowing the coolant, and obtaining the aspartame slurry are carried out continuously.

17. The method as defined in claim 1, wherein the aspartame solution is forcedly stirred during the cooling crystallization.

18. The method as defined in claim 17, wherein the aspartame solution is stirred by a stirrer comprising a shaft and a plurality of blades attached to the shaft.

19. The method as defined in claim 18, wherein the shaft rotates at about 0.1–10 rpm.

20. The method as defined in claim 19, wherein the shaft rotates at about 0.5–3 rpm.

21. The method as defined in claim 2 wherein temperature difference between the aspartame solution and the coolant is from about 5° C. to about 15° C.

22. The method as defined in claim 21 wherein the temperature difference between the aspartame solution and the coolant is from about 5 to about 7° C.

23. The method as defined in claim 2, wherein in the aspartame aqueous solution, aspartame is dissolved in water or water-immiscible organic solvent.

24. The method as defined in claim 2, wherein initial temperature of the aspartame solution is from about 30° C. to about 70° C.

25. The method as defined in claim 2, wherein the aspartame dissolved in the solution crystallizes and forms aspartame slurry as the cooling of the aspartame solution significantly proceeds.

26. The method as defined in claim 25, wherein temperature of the aspartame slurry obtained is about 20° C.

27. The method as defined in claim 26, wherein temperature of the aspartame slurry obtained is about 8° C.

28. The method as defined in claim 25, further comprising cooling the obtained aspartame slurry to further crystallize aspartame remaining dissolved in the slurry.

29. The method as defined in claim 2, wherein the coolant used is one selected from the group consisting of water, brine water, and aqueous solution of ethylene glycol or propylene glycol.

30. The method as defined in claim 25, wherein flowing the aspartame solution and obtaining the aspartame slurry are carried out continuously.

31. The method as defined in claim 2, wherein the aspartame solution is forcedly stirred during the cooling.

32. The method as defined in claim 31, wherein the aspartame solution is stirred by a stirrer comprising a shaft and a plurality of blades attached to the shaft.

33. The method as defined in claim 32, wherein the shaft rotates at about 0.1–10 rpm.

34. The method as defined in claim 33, wherein the shaft rotates at about 0.5–3 rpm.

* * * * *